US010047144B2

(12) United States Patent
Elson et al.

(10) Patent No.: US 10,047,144 B2
(45) Date of Patent: Aug. 14, 2018

(54) METHODS OF PURIFYING ANTIBODIES

(71) Applicant: NovImmune S.A., Geneva (CH)

(72) Inventors: Greg Elson, Collonges Sous Saleve (FR); Nicolas Fouque, Collonges Sous Saleve (FR); Jean-Francois Depoisier, Mont Saxonnet (FR); Nicolas Fischer, Geneva (CH); Giovanni Magistrelli, Cessay (FR)

(73) Assignee: NovImmune SA, Geneva (CH)

( * ) Notice: Subject to any disclaimer, the term of this patent is extended or adjusted under 35 U.S.C. 154(b) by 456 days.

(21) Appl. No.: 13/655,955

(22) Filed: Oct. 19, 2012

(65) Prior Publication Data

US 2013/0317200 A1 Nov. 28, 2013

Related U.S. Application Data

(60) Provisional application No. 61/548,958, filed on Oct. 19, 2011.

(51) Int. Cl.
C07K 16/46 (2006.01)
C07K 16/00 (2006.01)
C07K 16/24 (2006.01)
C07K 16/28 (2006.01)

(52) U.S. Cl.
CPC ............ *C07K 16/00* (2013.01); *C07K 16/248* (2013.01); *C07K 16/249* (2013.01); *C07K 16/2866* (2013.01); *C07K 16/468* (2013.01); *C07K 2317/32* (2013.01); *C07K 2317/52* (2013.01)

(58) Field of Classification Search
None
See application file for complete search history.

(56) References Cited

U.S. PATENT DOCUMENTS

| 4,745,183 | A | * | 5/1988 | Engelhorn et al. ......... 530/388.1 |
| 5,859,205 | A | * | 1/1999 | Adair et al. ................ 530/387.3 |
| 6,075,181 | A | | 6/2000 | Kucherlapati et al. |
| 6,150,584 | A | | 11/2000 | Kucherlapati et al. |
| 6,528,624 | B1 | | 4/2003 | Idusogie et al. |
| 2007/0259453 | A1 | * | 11/2007 | Engstrand et al. ........... 436/547 |
| 2009/0186396 | A1 | * | 7/2009 | Gagnon ...................... 435/235.1 |
| 2009/0191199 | A1 | | 7/2009 | Kanda et al. |
| 2009/0270596 | A1 | * | 10/2009 | Gagnon et al. ............. 530/387.1 |
| 2012/0156206 | A1 | * | 6/2012 | Hultberg ............ C07K 16/2863 424/136.1 |
| 2012/0184716 | A1 | | 7/2012 | Fischer et al. |
| 2013/0079272 | A1 | * | 3/2013 | Liu et al. ....................... 514/1.1 |
| 2014/0179547 | A1 | * | 6/2014 | Fischer ................ C07K 16/468 506/9 |

FOREIGN PATENT DOCUMENTS

| WO | WO 2008/086335 A2 | 7/2008 |
| WO | WO 2010/135558 | 11/2010 |
| WO | WO 2011/084255 | 7/2011 |
| WO | WO 2012/023053 | 2/2012 |
| WO | WO 2013/088259 | 6/2013 |

OTHER PUBLICATIONS

Rouet et al. "Bispecific antibodies with native chain structure" Nature Biotechnology 32(2), 2014, pp. 136-137.*
Eduardo Padlan, "Anatomy of the antibody molecule" Molecular Immun. 31(3) (1994), pp. 169-217.*
Rudikoff et al. "Single amino acid substitution altering antigen-binding specificity" Proc. Natl. Acad. Sci. USA, 79 (Mar. 1982), pp. 1979-1983.*
PhyNexus "About BAC CaptureSelect Resins from PhyTip columns" (2017, p. 1).*
Cole S. et al. "The EBV-Hybridoma Technique and its Application to Human Lung Cancer", *Monoclonal Antibodies and Cancer Therapy*, 1985, p. 77-96.
Cote R. et al. "Generation of human monoclonal antibodies reactive with cellular antigens", *Proc Natl Acad Sci USA*, 1983, vol. 80, p. 2026-2030.
Ford C. et al. "Affinity purification of novel bispecific antibodies recognizing carcinoembryonic antigen and doxorubicin", *Journal of Chromatography B: Biomedical Applications*, vol. 754, No. 2, 2001, p. 427-435.
Gupta S. et al. "Affinity chromatography and co-chromatography of bispecific monoclonal antibody immunoconjugates", *Journal of Biochemical and Biophysical Methods*, 2002, vol. 51, No. 3, p. 203-216.
Husereau D. R. et al.: "A general affinity method to purify peroxidase-tagged antibodies", *Journal of Immunological Methods*, 2001, vol. 249, No. 1-2, p. 33-41.
Kohler and Milstein, "Continuous cultures of fused cells secreting antibody of predefined specificity", *Nature*, 1975, vol. 256, p. 495-497.
Kozbor D. et al. "The production of monoclonal antibodies from human lymphocytes", *Immunology Today*, 1983, vol. 4, No. 3, p. 72-79.
Strohl W. R. "Optimization of Fc-mediated effector functions of monoclonal Antibodies", *Current Opinion in Biotechnology*, 2009, vol. 6, p. 685-91.

* cited by examiner

*Primary Examiner* — Daniel E Kolker
*Assistant Examiner* — James L Rogers
(74) *Attorney, Agent, or Firm* — Cooley LLP; Ivor R. Elrifi; Cynthia Kozakiewicz

(57) ABSTRACT

The invention provides methods of purifying antibodies using various antibody-specific purification media to rapidly and efficiently separate mixtures of antibodies, antibody fragments and/or antibody components to isolate a desired antibody product from the mixture. The invention relates to the purification of bispecific monoclonal antibodies carrying a different specificity for each binding site of the immunoglobulin molecule, e.g., antibodies composed of a single heavy chain and two different light chains, one containing a Kappa constant domain and the other a Lambda constant domain, including antibodies of different specificities that share a common heavy chain. The invention also provides the methods of efficiently purifying intact antibodies by separating the intact antibody from non-intact antibodies including free light chains.

8 Claims, 9 Drawing Sheets

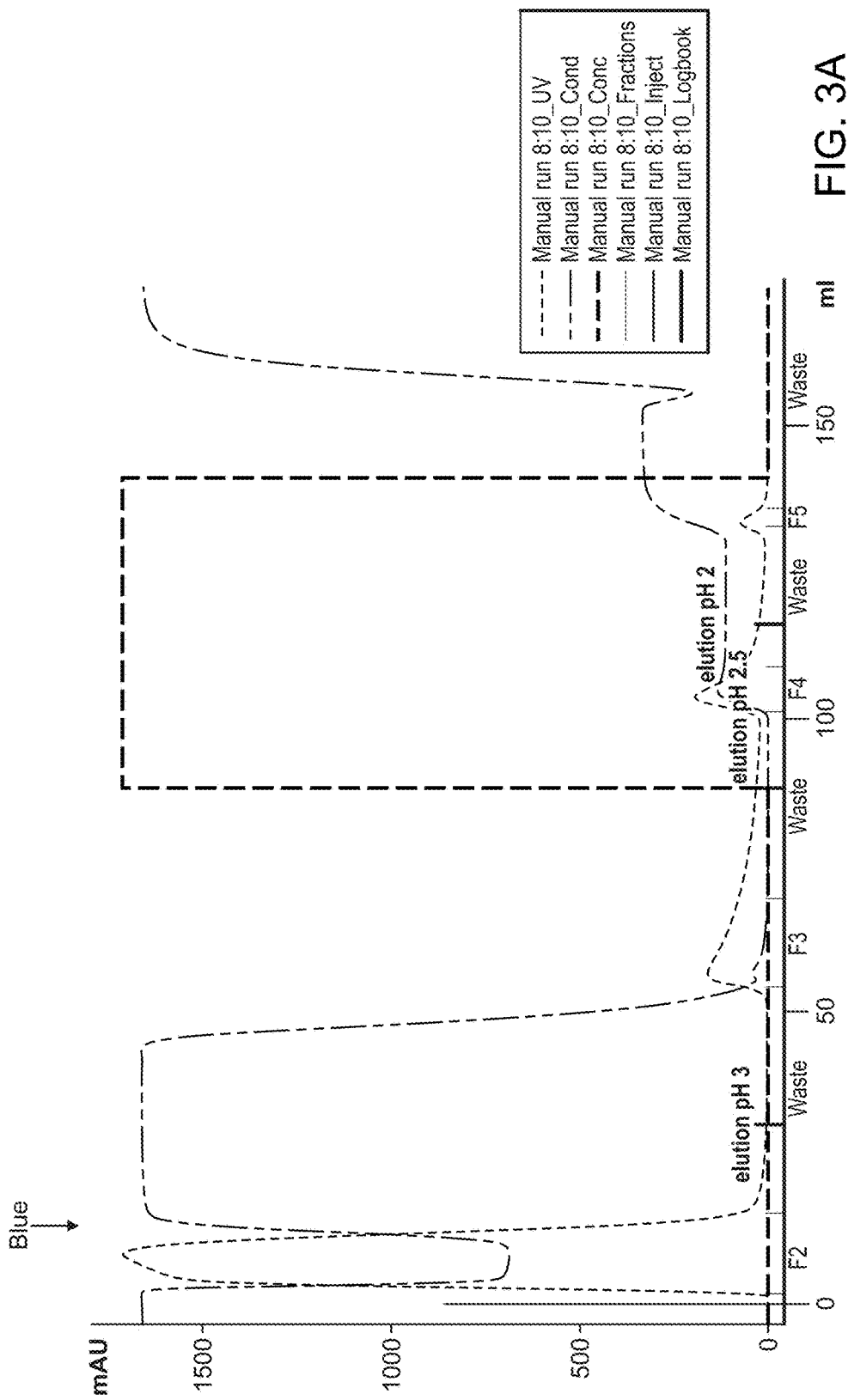

METHODS OF PURIFYING ANTIBODIES

RELATED APPLICATIONS

This application claims the benefit of and priority to U.S. Provisional Patent Application No. 61/548,958, filed Oct. 19, 2011, which is herein incorporated by reference in its entirety.

INCORPORATION OF SEQUENCE LISTING

The contents of the text file name "426001US_SeqList-.txt", which was created on Aug. 6, 2013 and is 10.0 KB in size, are hereby incorporated by reference in their entirety.

FIELD OF THE INVENTION

The invention provides methods of purifying antibodies using various antibody-specific affinity media to rapidly and efficiently separate mixtures of antibodies, antibody fragments and/or antibody components to isolate a desired antibody product from the mixture. The invention relates to the purification of bispecific monoclonal antibodies carrying a different specificity for each binding site of the immunoglobulin molecule, e.g., antibodies composed of a single heavy chain and two different light chains, one containing a Kappa constant domain and the other a Lambda constant domain, including antibodies of different specificities that share a common heavy chain. The invention also provides the methods of efficiently purifying intact antibodies by separating the intact antibody from free light chains produced during the antibody cell culture expression process.

BACKGROUND OF THE INVENTION

An antibody is composed of four polypeptides: two heavy chains and two light chains. The antigen binding portion of an antibody is formed by the light chain variable domain (VL) and the heavy chain variable domain (VH). At one extremity of these domains six loops form the antigen binding site and also referred to as the complementarity determining regions (CDR). Three CDRs are located on the VH domain (H1, H2 and H3) and the three others are on the VL domain (L1, L2 and L3).

The vast majority of immunoglobulins are bivalent and monospecific molecules carrying the same specificity on both arms as they are composed of two identical heavy chain polypeptides and two identical light chain polypeptides.

Monoclonal antibodies have emerged as a successful and attractive class of molecules for therapeutic intervention in several areas of human disease. However, targeting or neutralizing a single protein is not always sufficient to achieve efficacy in certain diseases which limits the therapeutic use of monoclonal antibodies. It is increasingly clear that in a number of indications neutralizing one component of a biological system is not sufficient to achieve efficacy. One solution to this problem is the co-administration of several monoclonal antibodies. This approach is however complicated by regulatory aspects if the antibodies to be combined have not been previously approved individually. Moreover, combination approaches are also costly from a manufacturing perspective. Accordingly, there exists a need for antibodies and therapeutics that enable targeting of multiple antigens with a single molecule, as well as a need for efficiently purifying and isolating these multi-specific antibodies. There also exists a need for efficiently purifying and isolating intact antibodies from mixtures that contain antibodies, antibody fragments and/or antibody components.

SUMMARY OF THE INVENTION

The invention provides a variety of techniques that use antibody-specific purification media and related reagents to separate and isolate a desired antibody product or combination of desired antibody products from a mixture of antibodies, antibody fragments, antibody components such as free light chains, and combinations thereof. The methods provided herein rapidly and efficiently separate a desired antibody product or combination of desired antibody products from a mixture of antibodies and/or fragments thereof. For example, in some embodiments, the methods are designed to isolate an intact antibody or a combination of intact antibodies from antibody components such as free light chains, which are a by-product of the antibody manufacturing process. As used herein, the term "intact" antibody molecule means a full-length antibody, as opposed to a fragment and/or other portion of a full-length antibody, which are referred to herein collectively as a "non-intact" antibody. The intact antibody can be any intact antibody, including by way of non-limiting example, intact monovalent antibodies, intact bispecific antibodies, intact multi-specific antibodies, intact monoclonal antibodies, such as intact fully human antibodies, intact humanized antibodies and/or other intact chimeric antibodies. In some embodiments, the methods are designed to isolate a bispecific antibody, such as, for example, bispecific antibodies that have a single heavy chain and at least one kappa (κ) light chain region (or light chain region derived from a κ light chain) and at least one lambda (λ) light chain region (or a light chain region derived from a λ light chain).

The purification medium is, in some embodiments, an affinity medium, for example, a resin or other separation means that is specific for κ light chains and portions thereof, such as KappaSelect resin and/or a Protein L-containing resin, which isolate antibodies and fragments thereof that contain a κ light chain (or a portion thereof). The purification medium is, in some embodiments, an affinity medium, for example, a resin or other separation means that is specific for λ light chains and portions thereof, such as LambdaFabSelect resin, which isolates antibodies and fragments thereof that contain a λ light chain (or a portion thereof). The purification medium is, for example, a mixed mode chromatography agent such as Mep HyperCel™ chromatography sorbent, which isolates intact IgG antibodies from antibody fragments and other antibody components, including free light chains. The purification media is, in some embodiments, a combination of one or more of these media.

In one aspect, the invention allows for the purification of bispecific antibodies and antigen-binding fragments thereof that are undistinguishable in sequence from standard antibodies. The unmodified nature of the purified antibodies and antigen-binding fragments thereof provides them with favorable manufacturing characteristics similar to standard monoclonal antibodies.

The methods provided herein are useful for purifying a variety of bispecific antibodies and antigen-binding fragments thereof, particularly the bispecific antibodies referred to herein as "κλ-bodies" and antigen-binding fragments thereof, which have a common IgG heavy chain and two different light chains, one having a kappa (κ) constant region and the other having a lambda (λ) constant region, that drive specificity for two independent targets.

The bispecific antibodies and antigen-binding fragments thereof to be purified can be generated using any of a variety of methods. For example, the bispecific antibodies and antigen-binding fragments thereof can be generated by (i) isolating two antibodies having different specificities and sharing the same variable heavy chain domain but different variable light chains, for example by using antibody libraries having a fixed heavy chain or transgenic animals containing a single VH gene; (ii) fusing the variable heavy chain domain to the constant region of a heavy chain, fusing one light chain variable domain to a Kappa constant domain, and fusing the other variable light chain domain to a Lambda constant domain; and (iii) co-expressing the three chains in a host cell or cell line, for example, mammalian cells and/or mammalian cell lines, leading to the assembly and secretion in the supernatant of a mixture of three antibodies: two monospecific antibodies and one bispecific antibody carrying two different light chains. In some antibodies and antigen-binding fragments thereof produced using this method, at least a first portion of the first light chain is of the Kappa type and at least a portion of the second light chain is of the Lambda type. In some antibodies and antigen-binding fragments thereof produced using this method, the first light chain includes at least a Kappa constant region. In some antibodies and antigen-binding fragments thereof produced using this method, the first light chain further includes a Kappa variable region. In some antibodies and antigen-binding fragments thereof produced using this method, the first light chain further includes a Lambda variable region. In some antibodies and antigen-binding fragments thereof produced using this method, the second light chain includes at least a Lambda constant region. In some antibodies and antigen-binding fragments thereof produced using this method, the second light chain further includes a Lambda variable region. In some antibodies and antigen-binding fragments thereof produced using this method, the second light chain further includes a Kappa variable region. In some antibodies and antigen-binding fragments thereof produced using this method, the first light chain includes a Kappa constant region and a Kappa variable region, and the second light chain includes a Lambda constant region and a Lambda variable region. In some antibodies and antigen-binding fragments thereof produced using this method, the constant and variable framework region sequences are human.

The bispecific antibodies and antigen-binding fragments thereof generated using this method or any other suitable method known in the art are purified using standard chromatography techniques used for antibody purification. The bispecific antibodies and antigen-binding fragments thereof generated using this method or any other suitable method known in the art can also be purified using other separation techniques, such as by way of non-limiting and non-exhaustive example, membrane filtration techniques and protein precipitation techniques. In a preferred embodiment, the bispecific antibody (or antibodies) and antigen-binding fragment(s) thereof is purified using affinity chromatography, for example KappaSelect affinity chromatography, LambdaFabSelect chromatography or Protein L affinity chromatography.

The invention provides methods of purifying a bispecific monoclonal antibody carrying a different specificity in each combining site and consisting of two copies of a single heavy chain polypeptide and a first light chain that includes a kappa constant region and a second light chain that includes a lambda constant region. These methods include the steps of: (i) providing a mixed antibody composition that includes one or more of the bispecific monoclonal antibodies carrying a different specificity in each combining site and consisting of two copies of a single heavy chain polypeptide and a first light chain that includes a kappa constant region and a second light chain that includes lambda constant region (bispecific MAb); one or more monospecific monoclonal antibodies having two lambda light chains or portions thereof (λ-MAb); and one or more monospecific monoclonal antibodies having two kappa light chains or portions thereof (κ-MAb); (ii) providing a separation means that has a specific affinity for a kappa light chain constant region or a lambda light chain constant region; (iii) contacting the separation means with the mixed antibody composition under conditions that allow for differential binding to the separation means by the bispecific MAb as compared to the binding to the separation means by the kappa light chain constant regions of the κ-MAb or by the lambda light chain constant regions of the λ-MAb; and (iv) eluting antibodies from the separation means under conditions that allow for preferential detachment of the bispecific MAb as compared to the detachment of the kappa light chain constant regions of the κ-MAb or the detachment of the lambda light chain constant regions of the λ-MAb.

In some embodiments, the separation means is a resin, a membrane, a magnetic bead, a particle or a monolith. In some embodiments, the separation means is coupled to a ligand having high specificity and affinity for a kappa light chain constant region or a lambda light chain constant region. In some embodiments, the separation means is a KappaSelect resin, a LambdaFabSelect resin, or a Protein L resin. In some embodiments, the ligand is an anti-lambda monoclonal antibody or an anti-kappa monoclonal antibody.

In some embodiments, the binding and/or elution conditions include a step variation in the pH level. In some embodiments, the binding and/or elution conditions include a step variation in the inorganic salt concentration such as sodium chloride (NaCl) concentration or the concentration of other inorganic salts such as by way of non-limiting and non-exhaustive example, inorganic salt combinations from the Hofmeister series of ions. In some embodiments, the binding and/or elution conditions include a step variation in the concentration of an amino acid in the composition, such as by way of non-limiting and non-exhaustive example, the concentration of arginine, histidine, proline, phenylalanine, tyrosine, tryptophan and/or glycine. In some embodiments, the binding and/or elution conditions include one or more mild denaturing agents such as by way of non-limiting and non-exhaustive example, Polysorbate 20, Polysorbate 80, Polyethylene glycol 2000, Polyethylene glycol 8000, Triton X-100, CHAPS, NP-40, and other ionic, non-ionic and/or zwitterionic surfactants.

In some embodiments, the methods comprise the further step of determining the purity and proportions of bispecific antibody, κ-MAb and/or λ MAb in the eluted fraction. This step can be accomplished using any of a variety of art-recognized techniques, such as by way of non-limiting and non-exhaustive example, hydrophobic interaction-high performance liquid chromatography (HIC-HPLC), ion exchange-high performance liquid chromatography (IEX-HPLC) or reverse phase-high performance liquid chromatography (RP-HPLC).

The Example provided herein demonstrates the feasibility of using a higher pH step elution to preferentially elute bispecific κλ-body product from KappaSelect affinity resin over monospecific κ-MAb which elutes at a lower pH, as the monospecific MAb presumably has a higher affinity to the resin owing to the presence of two κ chains in the monospecific format as opposed to a single κ chain in the κλ-body. The methods described herein are useful in other chromatography supports where affinity towards the light chain is used to differentially bind the monospecific and/or bi-specific products, such as, by way of non-limiting and non-exhaustive example, LambdaFabSelect, ion-exchange, hydrophobic interaction, and mixed mode resins (e.g., hydroxyapatite) and other chromatography techniques. Those of ordinary skill in the art will readily appreciate other art-recognized techniques that would fall within this category. Elution strategies to separate the different products should not only be limited to pH variation, but could also encompass, by way of non-limiting and non-exhaustive example, cation-exchange separation techniques using step variation of salt concentration such as NaCl concentration or the concentration of other inorganic salts (e.g., inorganic salt combinations from the Hofineister series of ions), Arginine and other amino acids such as histidine, proline, phenylalanine, tyrosine, tryptophan, and glycine concentration, use of mild denaturing agents such as, for example, Polysorbate 20, Polysorbate 80, Polyethylene glycol 2000, Polyethylene glycol 8000, Triton X-100, CHAPS, NP-40, and other ionic, non-ionic and/or zwitterionic surfactants, and so on.

In another aspect, the present invention relates to the efficient removal of free light chains from intact antibodies, including monospecific antibodies, bispecific antibodies and mixtures of intact antibodies. In particular, chromatography conditions have been identified that are applicable for isolating intact bispecific or monospecific monoclonal antibodies or combinations of intact bispecific or monospecific monoclonal antibodies from free light chains.

The Example provided herein uses a bispecific antibody for the mixed mode affinity isolation of intact IgG molecules from a mixture that contains free light chains. It is to be understood that this is merely an example, and the methods provided herein are useful in conjunction with any antibody manufacturing process that generates incomplete antibody components (i.e., non-intact antibodies) that can be present as monomers or polymers, and in native or altered conformation. In addition, while the examples provided herein use a purification medium that identifies intact IgG antibodies, it is to be understood that these methods can be used with any purification media that identify other intact antibody molecules.

The intact antibody molecules generated using any suitable method known in the art can be purified using the mixed mode chromatography separation techniques provided herein alone or in conjunction with any other suitable separation techniques, such as by way of non-limiting and non-exhaustive example, membrane filtration techniques and protein precipitation techniques.

The invention provides methods of purifying an intact antibody or a combination of intact antibodies from a mixture that contains non-intact antibodies, including antibody components, dimers of antibody components, antibody fragments and/or combinations thereof. The combination of intact antibodies can include one or more different types of intact antibodies, including antibodies that bind the same or different targets. The intact antibody can be any intact antibody, including by way of non-limiting example, intact monovalent antibodies, intact bispecific antibodies, intact multi-specific antibodies, intact monoclonal antibodies, such as intact fully human antibodies, intact humanized antibodies and/or other intact chimeric antibodies. The combination of intact antibodies can include any combination of intact antibodies to the same or different targets, including by way of non-limiting example, combinations that include one or more of the following: intact monovalent antibodies, intact bispecific antibodies, intact multi-specific antibodies, intact monoclonal antibodies, intact fully human antibodies, intact humanized antibodies and/or other intact chimeric antibodies.

In some embodiments, these methods include the steps of: (i) providing a mixed antibody composition that includes one or more of the intact antibodies or a combination of intact antibodies and one or more non-intact antibody molecules, including one or more antibody components such as a free light chain, one or more dimers of an antibody component such as a free light chain, and/or one or more antibody fragments; (ii) providing a separation means that has a differential affinity between an intact antibody molecule as compared to the non-intact antibody molecule; (iii) contacting the separation means with the mixed antibody composition under conditions that allow for differential binding to the separation means by the intact antibody molecule or combination of intact antibodies as compared to the binding to the separation means by non-intact antibody molecule (e.g., one or more antibody components such as a free light chain, one or more dimers of an antibody component such as a free light chain, and/or one or more antibody fragments); and (iv) separating the intact antibody or combination of intact antibodies from the separation means and retaining the intact antibody or combination of intact antibodies, thereby purifying the intact antibody or combination of intact antibodies from the mixed antibody composition. In some embodiments, the intact antibody or combination of intact antibodies is separated from the separation means by eluting the intact antibody or combination of intact antibodies from the separation means under conditions that allow for preferential detachment of the intact antibody or combination of intact antibodies as compared to the detachment of the non-intact antibody molecule (e.g., one or more antibody components such as a free light chain, one or more dimers of an antibody component such as a free light chain, and/or one or more antibody fragments). In some embodiments, the separation means is contacted by the antibody mixture composition under conditions that allow for binding by the intact antibody or combination of intact antibodies to the separation means, but do not allow for binding between the non-intact antibody molecule and the separation means. In some embodiments, the intact antibody or combination of intact antibodies is separated from the non-intact antibody fraction by removing any unbound, non-intact antibodies from the mixed antibody composition or by allowing the unbound, non-intact antibodies to flow through the separation means and discarding or otherwise removing the unbound fraction. In some embodiments, the non-intact antibody molecule is a free light chain.

In some embodiments, the separation means is a resin, a membrane, a magnetic bead, a particle or a monolith. In some embodiments, the separation means is coupled to a ligand having differential specificity and affinity for an intact antibody molecule as compared to a non-intact antibody molecule. In some embodiments, the separation means is a mixed mode chromatography medium, such as, for example, hydrophobic interaction-high performance liquid chromatography (HIC-HPLC) or ion exchange-high performance liquid chromatography (IEX-HPLC). In some embodiments, the mixed mode chromatography medium is Mep HyperCel™ Other mixed mode chromatography media include, for example, Capto™ MMC, Capto™ adhere, HEA HyperCel™, PPA HyperCel™, CHT™ ceramic hydroxyapatite, and Nuvia™ cPrime™. In some embodiments, the ligand is an anti-antibody monoclonal antibody such as, for example, an anti-IgG antibody.

In some embodiments, the methods comprise the further step of determining the purity and proportions of the intact antibody in the eluted fraction. This step can be accomplished using any of a variety of art-recognized techniques, such as by way of non-limiting and non-exhaustive example, size exclusion-high performance liquid chromatography (SEC-HPLC), hydrophobic interaction-high performance liquid chromatography (HIC-HPLC), ion exchange-high performance liquid chromatography (IEX-HPLC), or reverse phase-high performance liquid chromatography (RP-HPLC).

In some embodiments, these methods include the steps of: (i) providing a mixed antibody composition that includes one or more of the intact antibodies or a combination of intact antibodies and one or more non-intact antibody molecules, including one or more antibody components such as a free light chain, one or more dimers of an antibody component such as a free light chain, and/or one or more antibody fragments; (ii) providing a separation means that has a differential affinity between a non-intact antibody molecule as compared to an intact antibody molecule; (iii) contacting the separation means with the mixed antibody composition under conditions that allow for binding to the separation means by the non-intact antibody molecule but do not allow for binding to the separation means by the intact antibody or combination of intact antibodies such that the intact antibody or combination of intact antibodies remain in an unbound fraction; and (iv) retaining the unbound fraction that includes the intact antibody or combination of intact antibodies. In some embodiments, the methods may include the additional step of separating the non-intact antibody molecule from the separation means. In some embodiments, the non-intact antibody molecule is a free light chain.

In some embodiments, the separation means is a resin, a membrane, a magnetic bead, a particle or a monolith. In some embodiments, the separation means is coupled to a ligand having differential specificity and affinity for an intact antibody molecule. In some embodiments, the separation means is a mixed mode chromatography medium, such as, for example, hydrophobic interaction-high performance liquid chromatography (HIC-HPLC) or ion exchange-high performance liquid chromatography (IEX-HPLC). In some embodiments, the mixed mode chromatography medium is Mep HyperCel™. Other mixed mode chromatography media include, for example, Capto™ MMC, Capto™ adhere, HEA HyperCel™, PPA HyperCel™, CHT™ ceramic hydroxyapatite, and Nuvia™ cPrime™. In some embodiments, the ligand is an anti-antibody monoclonal antibody such as, for example, an anti-IgG antibody.

In some embodiments, the methods comprise the further step of determining the purity and proportions of the intact antibody in the eluted fraction. This step can be accomplished using any of a variety of art-recognized techniques, such as by way of non-limiting and non-exhaustive example, size exclusion-high performance liquid chromatography (SEC-HPLC), hydrophobic interaction-high performance liquid chromatography (HIC-HPLC), ion exchange-high performance liquid chromatography (IEX-HPLC), or reverse phase-high performance liquid chromatography (RP-HPLC).

BRIEF DESCRIPTION OF THE DRAWINGS

FIG. 1A. Kappa variable domain fused to a Kappa constant domain and Lambda variable domain fused to Lambda constant domain. FIG. 1B. Kappa variable domains fused to a Kappa constant domain and a Lambda constant domain. FIG. 1C. Lambda variable domains fused to a Kappa constant domain and a Lambda constant domain.

FIG. 3A is a graph depicting a representative UV-trace profile of KappaSelect affinity chromatography using step pH elution.

DETAILED DESCRIPTION

The invention provides a variety of techniques that use antibody-specific affinity media and related reagents to separate and isolate a desired antibody product from a mixture of antibodies, antibody fragments, antibody components such as free light chains, and combinations thereof. The methods provided herein rapidly and efficiently separate a desired antibody product from a mixture of antibodies and/or fragments thereof.

Figure 1A:
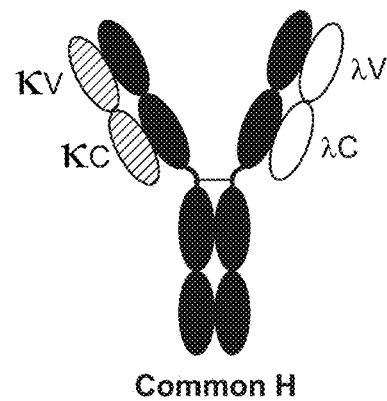
FIGS. 1A-1C are a schematic representation of the structure of different κλ-body bispecific antibodies composed of two copies of a unique heavy chain polypeptide and two different light chain polypeptides. The locations and/or arrangements of the Kappa light chain and the Lambda light chain (or portions thereof) shown in these figures are not intended to be limiting. Those of ordinary skill in the art will appreciate that the Kappa light chain and the Lambda light chain (or portions thereof) can also be arranged so as to produce the mirror-image of the bispecific antibodies shown in FIGS. 1A-1C. Those of ordinary skill in the art will also appreciate that the bispecific antibodies that are represented in a full IgG format in FIGS. 1A-1C can also be generated using other immunoglobulin isotypes or in other immunoglobulin formats such as F(ab')$_2$.
Figure 1B:
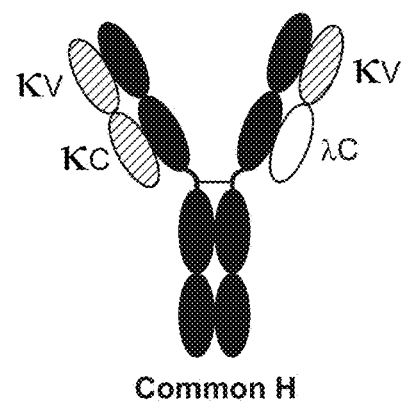
Figure 1C:
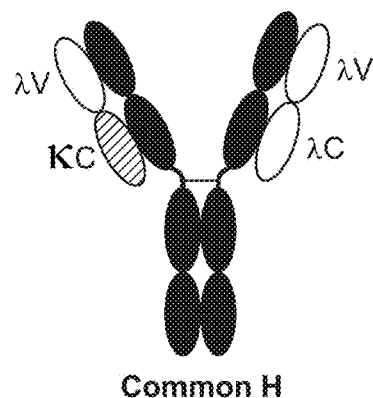

The present invention provides methods of purifying bispecific antibodies that are identical in structure to a human immunoglobulin. This type of molecule is composed of two copies of a unique heavy chain polypeptide, a first light chain variable region fused to a constant Kappa domain and second light chain variable region fused to a constant Lambda domain. Each combining site displays a different antigen specificity to which both the heavy and light chain contribute. The light chain variable regions can be of the Lambda or Kappa family and are preferably fused to a Lambda and Kappa constant domain, respectively. This is preferred in order to avoid the generation of non-natural polypeptide junctions. However it is also possible to obtain bispecific antibodies of the invention by fusing a Kappa light chain variable domain to a constant Lambda domain for a first specificity and fusing a Lambda light chain variable domain to a constant Kappa domain for the second specificity (FIG. 1). The bispecific antibodies described herein are also referred to as IgGKX antibodies or "κλ-bodies," a fully human bispecific IgG format. This κλ-body format allows the affinity purification of a bispecific antibody that is indistinguishable from a standard monoclonal antibody, e.g., a standard IgG molecule, therefore, favorable as compared to previous formats.

The κλ-bodies are generated by identifying two antibody Fv regions (each composed by a variable light chain and variable heavy chain domain) having different antigen specificities that share the same heavy chain variable domain.

The present invention also provides methods of purifying intact antibodies from mixtures that contain non-intact antibody molecules, including, for example, antibody components, dimers of antibody components, antibody fragments and/or combinations thereof.

The κλ-bodies and/or intact antibodies to be purified using the methods of the invention are generated using any of a variety of methods for generating antibodies. Numerous methods have been described for the generation of monoclonal antibodies and fragments thereof. (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the sequence of both the light chain and the heavy chain, including the CDRs 1 and 2, arise from human genes. The CDR3 region can be of human origin or designed by synthetic means. Such antibodies are termed "human antibodies" or "fully human antibodies" herein. Human monoclonal antibodies can be prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Monoclonal antibodies are generated, e.g., by immunizing an animal with a target antigen or an immunogenic fragment, derivative or variant thereof. Alternatively, the animal is immunized with cells transfected with a vector containing a nucleic acid molecule encoding the target antigen, such that the target antigen is expressed and associated with the surface of the transfected cells. A variety of techniques are well-known in the art for producing xenogenic non-human animals. For example, see U.S. Pat. Nos. 6,075,181 and 6,150,584, which is hereby incorporated by reference in its entirety.

Alternatively, the antibodies are obtained by screening a library that contains antibody or antigen binding domain sequences for binding to the target antigen. This library is prepared, e.g., in bacteriophage as protein or peptide fusions to a bacteriophage coat protein that is expressed on the surface of assembled phage particles and the encoding DNA sequences contained within the phage particles (i.e., "phage displayed library").

Hybridomas resulting from myeloma/B cell fusions are then screened for reactivity to the target antigen. Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Although not strictly impossible, the serendipitous identification of different antibodies having the same heavy chain variable domain but directed against different antigens is highly unlikely. Indeed, in most cases the heavy chain contributes largely to the antigen binding surface and is also the most variable in sequence. In particular, the CDR3 on the heavy chain is the most diverse CDR in sequence, length and structure. Thus, two antibodies specific for different antigens will almost invariably carry different heavy chain variable domains.

In some embodiments, the κλ-bodies and/or intact antibodies to be purified are generated, for example, using antibody libraries in which the heavy chain variable domain is the same for all the library members and thus the diversity is confined to the light chain variable domain. Such libraries are described, for example, in co-pending application PCT/US2010/035619, filed May 20, 2010 and published on Nov. 25, 2010 as PCT Publication No. WO 2010/135558 and co-pending application PCT/US2010/057780, filed Nov. 23, 2010 and published on Jul. 14, 2011 as PCT Publication No. WO 2011/084255, each of which is hereby incorporated by reference in its entirety. However, as the light chain variable domain is expressed in conjunction with the heavy variable domain, both domains can contribute to antigen binding. To further facilitate the process, antibody libraries containing the same heavy chain variable domain and either a diversity of Lambda variable light chains or Kappa variable light chains can be used in parallel for in vitro selection of antibodies against different antigens. This approach enables the identification of two antibodies having a common heavy chain but one carrying a Lambda light chain variable domain and the other a Kappa light chain variable domain that can be used as building blocks for the generation of a bispecific antibody in the full immunoglobulin format of the invention. The bispecific antibodies to be purified using the methods of the invention can be of different isotypes and their Fc portion can be modified in order to alter the bind properties to different Fc receptors and in this way modify the effectors functions of the antibody as well as it pharmacokinetic properties. Numerous methods for the modification of the Fc portion have been described and are applicable to antibodies of the invention. (See for example Strohl, WR Curr Opin Biotechnol 2009 (6):685-91; U.S. Pat. No. 6,528,624; U.S. Patent Application Publication No. 2009/0191199 filed Jan. 9, 2009). The methods of the invention can also be used to purify bispecific antibodies and antibody mixtures in a F(ab')2 format that lacks the Fc portion.

Preferably, the κλ-bodies to be purified have been optimized for the co-expression of the common heavy chain and two different light chains into a single cell to allow for the assembly of a bispecific antibody of the invention. If all the polypeptides get expressed at the same level and get assembled equally well to form an immunoglobulin molecule then the ratio of monospecific (same light chains) and bispecific (two different light chains) should be 50%. However, it is likely that different light chains are expressed at different levels and/or do not assemble with the same efficiency. Furthermore, light chains that escape assembly into an intact IgG molecule may be secreted into the cell culture supernatant as "free-light chains" (FLCs). Means to modulate the relative expression of the different polypeptides to compensate for their intrinsic expression characteristics or different propensities to assemble with the common heavy chain include, by way of non-limiting examples, the use of promoter(s) with variable strength(s), the use of internal ribosome entry sites (IRES) featuring different efficiencies or other types of regulatory elements that can act at transcriptional or translational levels as well as acting on mRNA stability. The modulation of the expression can also be achieved by multiple sequential transfections of cells to increase the copy number of individual genes expressing one or the other light chain and thus modify their relative expressions.

The co-expression of the heavy chain and two light chains generates a mixture of three different antibodies secreted into the cell culture supernatant: two monospecific bivalent antibodies and one bispecific bivalent antibody. The latter has to be purified from the mixture to obtain the κλ-body of interest. The purification methods described herein greatly facilitate the purification procedure by the use of affinity chromatography media that specifically interact with the Kappa or Lambda light chain constant domains such as KappaSelect affinity medium, LambdaFabSelect affinity medium, and/or the Protein L, CaptureSelect Fab Kappa and CaptureSelect Fab Lambda affinity matrices. This affinity chromatography purification approach is efficient and generally applicable to bispecific antibodies, including κλ-bodies. This is in sharp contrast with specific purification methods that have to be developed and optimized for each bispecific antibody derived from quadromas or other cell lines expressing antibody mixtures. Indeed, if the biochemical characteristics of the different antibodies in the mixtures are similar, their separation using standard chromatography technique such as ion exchange chromatography can be challenging or not possible at all.

The co-expression of the three chains led to the assembly of three different antibodies: two monospecific and one bispecific antibodies. Their theoretical relative ratios should be 1:1:2 provided the expression levels and assembly rates are similar for both light chains. The bispecific antibodies were purified using affinity chromatography procedures that preferentially elute the bispecific antibodies, such as the κλ-bodies, using affinity resins.

The co-expression of the three chains also led to the generation of excess free light chain in the cell culture supernatant. Such free light chains can be potentially problematic to remove in purification processes omitting, for example, protein A affinity chromatography. Free-light chains could be efficiently separated from the intact antibody mix using mixed-mode chromatography as demonstrated herein.

Previous approaches to produce and purify bispecific antibody formats aimed at forcing the production of a homogenous bispecific molecule using different antibody engineering approaches were done at the expense of productivity, scalability and stability of the product. The methods described herein provide efficient and generic means to purify the bispecific antibody from a mixture containing monovalent, monoclonal antibodies and free light chains.

EXAMPLES

Example 1

Purification of Bispecific Antibodies Carrying a Lambda and a Kappa Light Chain

The κλ-body is a novel bi-specific IgG format that comprising a common IgG1 heavy chain and two different light chains that drive specificity for two independent targets. In order to allow for an efficient purification protocol applicable to large scale industrial processes, the format requires that one light chain contains a κ constant region whilst the other contains a λ constant region. (See FIG. 1).

Figure 2:
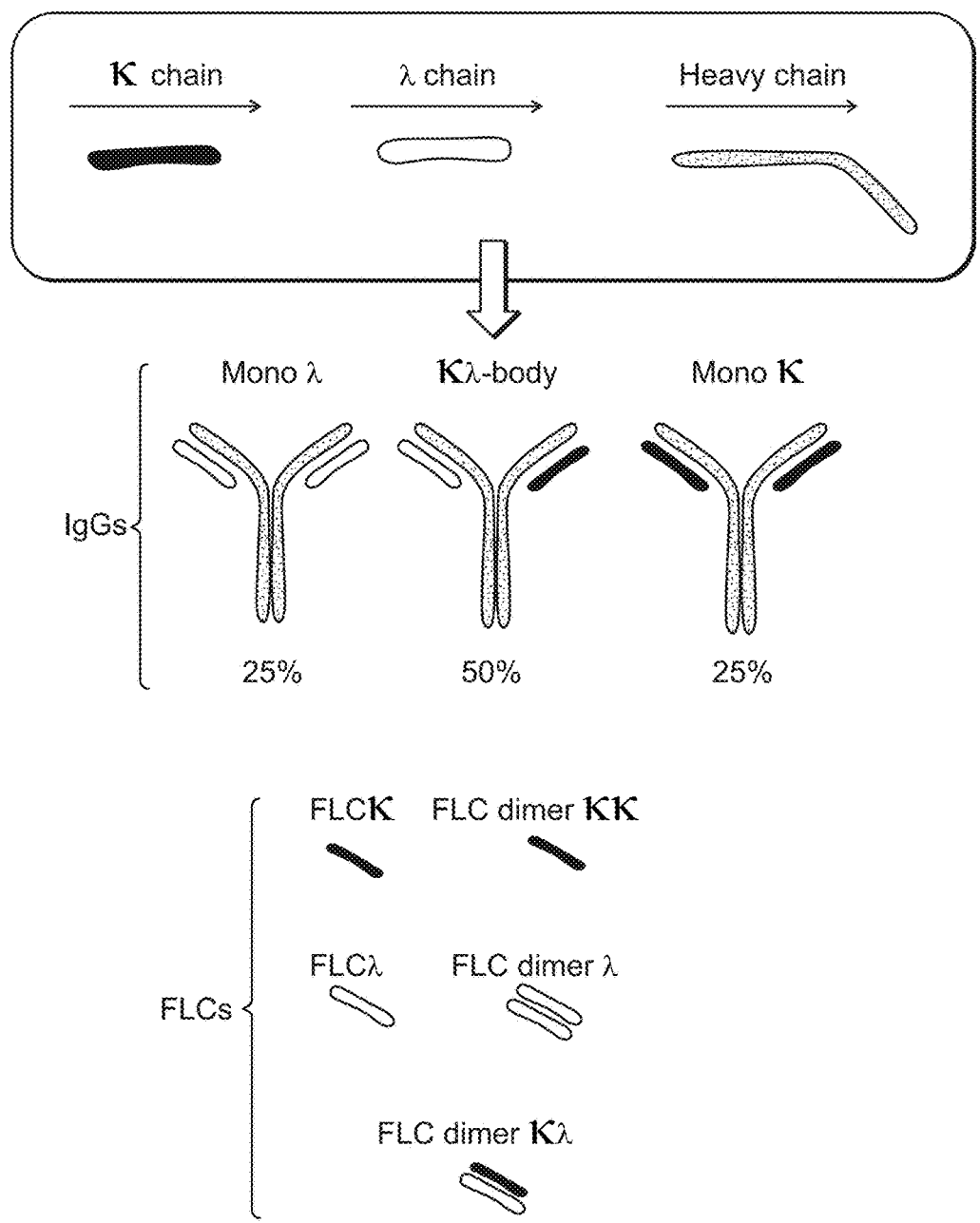
FIG. 2 is an illustration depicting that the expression of tri-cistronic expression vector in CHO cells gives rise to three antibody products with a theoretical 25:50:25 ratio for the IgG products (middle panel labeled "IgGs") and a mixture of free light chains (FLCs) and dimers of these FLCs (lower panel labeled "FLCs").

In order to produce κλ-body, the common heavy chain and two light chains are expressed in CHO cells using a tri-cistronic expression vector. This vector format allows for the construction of three products: monospecific κ monoclonal antibody (MAb), bispecific κλ-body and monospecific λ-MAb. Assuming similar expression levels and assembly with the heavy chain between Kappa and Lambda light chains, the theoretical product ratio is 25:50:25 in addition to free light chains. (See FIG. 2).

Purification of this κλ-body format can be performed by sequential binding to KappaSelect and LambdaFabSelect affinity resins (GE Healthcare), as described for example, in co-pending U.S. application Ser. No. 13/210,723, filed on Aug. 16, 2011. These resins are coupled with domain ligands having high specificity and affinity for either the κ or λ constant region. However, there exists a need for improved and cost-effective purification processes that allow for large scale purification of the κλ-bodies and other bispecific antibodies. Removal of the protein A affinity supernatant capture step is envisioned and possible as long as a free light chains can be removed from the mixture prior to KappaSelect and LambdaFabSelect affinity chromatography.

With the aim of streamlining the purification process, it was hypothesized that the κλ-body would bind to either KappaSelect or LambdaFabSelect resins with a weaker affinity than the corresponding monospecific κ-MAb (for KappaSelect) or monospecific λ-MAb (for LambdaFabSelect) by-product due to the fact that it contains only one of each light chain rather than two for the monoclonal format (either κ or λ). Furthermore, it was hypothesized that free light chains could be separated from intact antibody using mixed mode chromatography to directly capture recombinant protein from the supernatant. (See FIG. 2).

The studies provided herein demonstrate the successful separation of κλ-body from monospecific kappa Ab using step pH elution during either KappaSelect or LambdaFabSelect affinity chromatography.

Start Material: For KappaSelect chromatography, the clarified 25 L wave bag fermentation supernatant of a CHO cell transfected with a κλ bispecific expression vector (containing one γ1 heavy chain cDNA, one κ light chain cDNA and one λ light chain cDNA) was used as the starting material for purification. For LambdaFabSelect and mixed mode chromatography, the clarified supernatant of a BIOSTAT CultiBag STR 100 L fermentation of a CHO cell transfected with a κλ bispecific expression vector (containing one γ1 heavy chain cDNA, one κ light chain cDNA and one λ light chain cDNA) was used as the starting material for purification.

KappaSelect Chromatography Step: An anti-IFNγ/IL-6RC (i.e., IL-6RC is the complex formed between IL-6 and IL-6R) κλ-body bispecific IgG antibody was purified using KappaSelect affinity chromatography media (GE Healthcare). The heavy and light chain amino acid sequences of the anti-IFNγ/IL-6RC κλ-body bispecific IgG antibody are shown below:

```
Anti-IL6RC VKappa light chain
                                                    (SEQ ID NO: 4)
EIVLTQSPATLSLSPGERATLSCRASQSVSSYLAWYQQKPGQAPRLLIYDASNRATGIPARFSG
SGSGTDFTLTISSLEPEDFAVYYCQQWLPTTPATFGQGTKVEIKRTVAAPSVFIFPPSDEQLKS
GTASVVCLLNNFYPREAKVQWKVDNALQSGNSQESVTEQDSKDSTYSLSSTLTLSKADYEKHKV
YACEVTHQGLSSPVTKSFNRGEC Anti-IFNγ VLambda light chain
                                                    (SEQ ID NO: 5)
NFMLTQPHSVSESPGKTVTISCTRSSGSIASNYVQWYQQRPGSSPTTVIYEDNQRPSGVPDRFS
GSIDSSSNSASLTISGLKTEDEADYYCQSQSWDGNHIVFGGGTKLTVLGQPKAAPSVTLFPPSS
EELQANKATLVCLISDFYPGAVTVAWKADSSPVKAGVETTTPSKQSNNKYAASSYLSLTPEQWK
SHRSYSCQVTHEGSTVEKTVAPTECS Common heavy chain
                                                    (SEQ ID NO: 6)
EVQLLESGGGLVQPGGSLRLSCAASGFTFSSYAMSWVRQAPGKGLEWVSAISGSGGSTYYADSV
KGRFTISRDNSKNTLYLQMNSLRAEDTAVYYCAKSYGAFDYWGQGTLVTVSSASTKGPSVFPLA
PSSKSTSGGTAALGCLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPG.
```

After column loading at 10 mg/mL and a wash step with 50 mM Sodium Phosphate, 250 mM Sodium Chloride, pH 7.0 (5 column volumes), a pH step-elution (pH 3.0 followed by pH 2.5 and pH 2.0) was performed using a 50 mM glycine buffer adjusted to the relevant pH. The flow through (F/T) and eluted fractions were collected and analyzed by absorbance measurement at 280 nm (using a NanoDrop UV-Vis spectrophotometer, Thermo Scientific) in order to determine product recovery, reduced and non-reduced SDS-PAGE (using Invitrogen Novex NuPAGE 12-well 4-20% gradient gels following manufacturer's guidelines) in order to determine the purity and composition of the samples and ion exchange-high performance liquid chromatography (IEX-HPLC; method described below) in order to determine the ability of the purification process to separate the κλ-body bispecific IgG from the two monospecific antibody by-products.

IEX-HPLC method: This Ion Exchange-High Performance Liquid Chromatography (IEX-HPLC) method was used to determine the proportions of monospecific and bispecific antibody in purified samples. The IEX-HPLC method allows for the separation of protein variants according to their charge distribution. Samples were prepared to load 50 μg onto A BioMab NP5-SS column (Agilent) and a linear gradient of 10 mM sodium phosphate, 500 mM NaCl, pH 6.5 (from 0% to 100% NaCl concentration) at a flow rate of 0.8 mL/min was applied in order to separate the different antibody products. UV detection at 214 nm was employed to monitor sample elution. The three populations were identified (according to reference standards) and analyzed according to their percentage relative area. The percentage of each isoform was determined by calculating the peak area of each component relative to the total peak area.

Figure 3B:
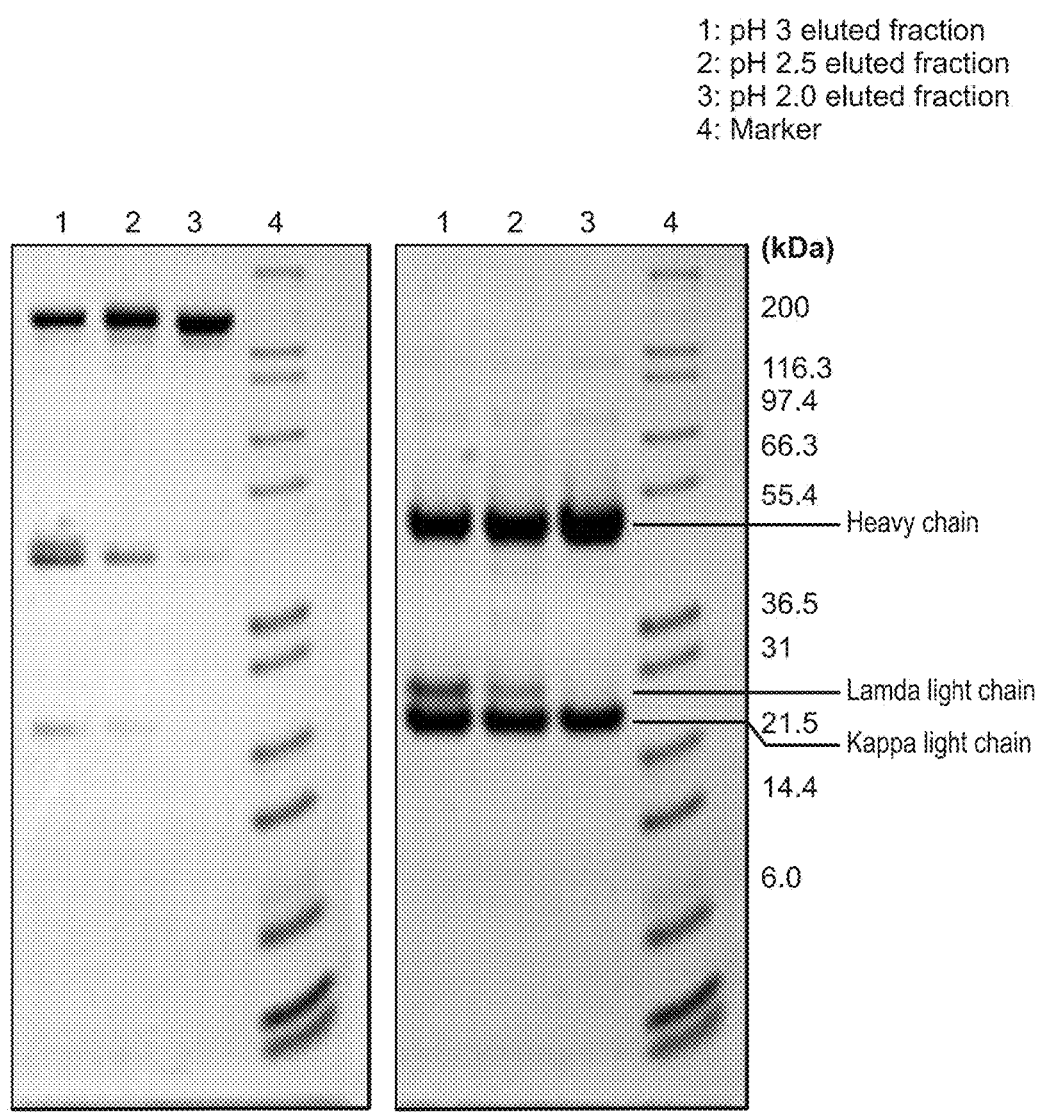
FIG. 3B is an illustration depicting non-reduced and reduced SDS-PAGE of KappaSelect elution fractions.
Figure 3C:
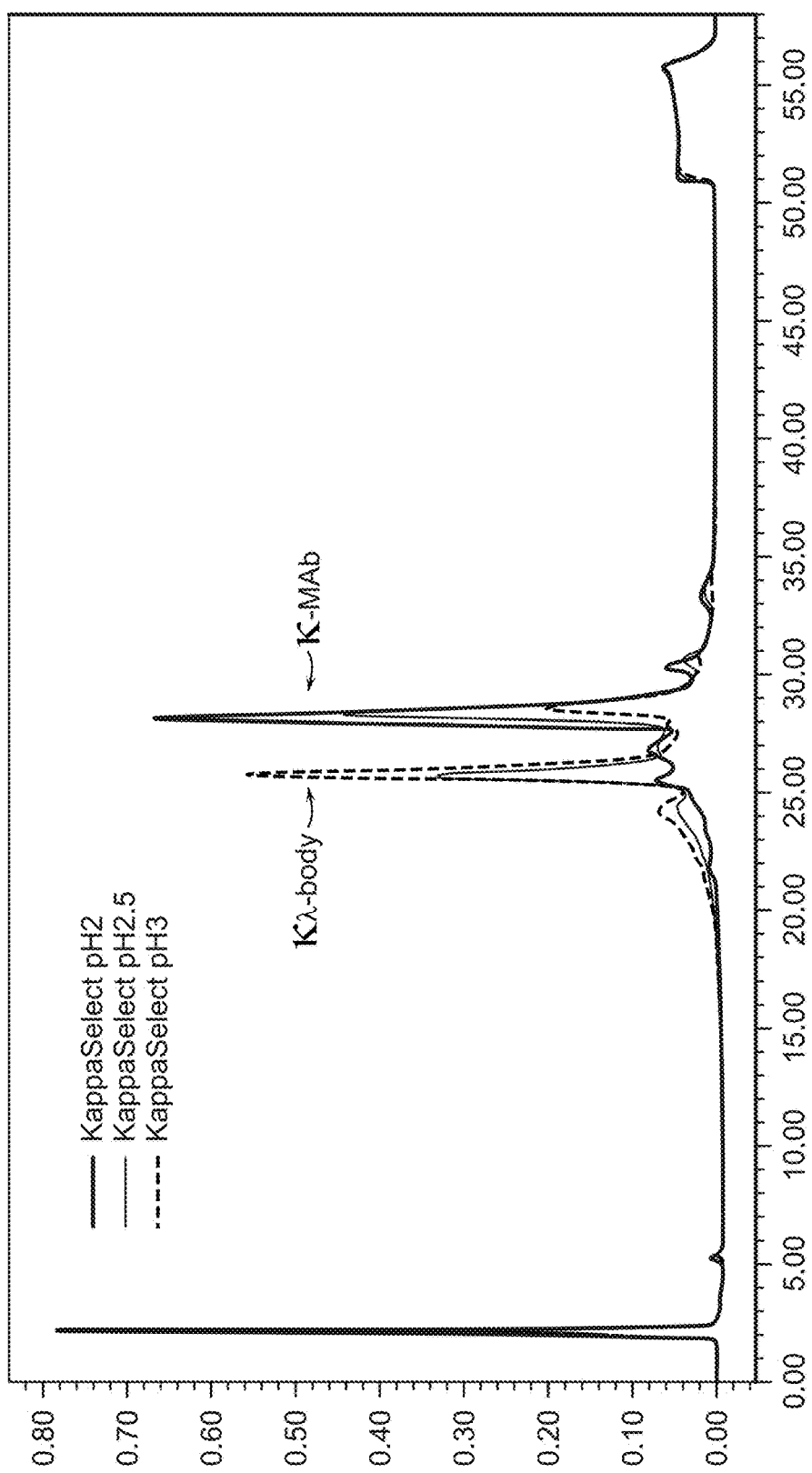
FIG. 3C is a graph depicting IEX-HPLC analysis of KappaSelect elution fractions.

As shown by the UV trace (blue) in FIG. 3A, the three pH step elutions applied to the KappaSelect chromatography resin allowed for the sequential isolation of three bound fractions. Non-reduced SDS-PAGE analysis, shown in FIG. 3B revealed the high purity of the eluted fractions containing assembled full length antibodies as anticipated. Some free light chain products (monomer and dimer forms) were also detected. Reduced SDS-PAGE analysis suggested that the consecutive pH elution steps lead to the differential retention of the κλ-body relatively to the two monospecific antibodies, based on light chain composition. The eluting fraction at pH3.0 contained equivalent levels of both light chains whereas the pH 2.5 and pH 2.0 fractions presented minimal or no detectable levels of λ light chain. The three bound fractions were further characterized by integrating the peak areas of the IEX-HPLC chromatograms (FIG. 3C). The results summarized in Table 1 were in accordance with the SDS-PAGE analysis, demonstrating the vast abundance of the κλ-body (70.10%) in the first eluted fraction at pH 3.0. Subsequent elution steps at pH 2.5 and pH 2.0 resulted in the elution of the monospecific κ antibody. A pH step elution strategy with the KappaSelect resin was therefore shown to effectively separate bispecific κλ-body from monospecific κ- and λ-MAb.

TABLE 1

UV peak integration of IEX-HPLC analysis of Kappa Select bound fractions

| | % area | |
|---|---|---|
| Samples | mono-k | κλ-body |
| KappaSelect pH 3.0 | 29.90 | 70.10 |
| KappaSelect pH 2.5 | 58.65 | 41.35 |
| KappaSelect pH 2.0 | 89.01 | 10.99 |

This data demonstrates the feasibility of using a higher pH step elution to preferentially elute bispecific κλ-body product from KappaSelect affinity resin over monospecific κ-MAb which elutes at a lower pH. This is presumably due to a higher affinity to the resin owing to the presence of two κ chains in the monospecific format as opposed a single κ chain in the κλ-body.

Thus, this separation is also useful in other chromatography supports where affinity towards the light chain is used to differentially bind the monospecific and/or bi-specific products, such as, by way of non-limiting and non-exhaustive example, LambdaFabSelect, ion-exchange, hydrophobic interaction, and mixed mode resins (e.g., hydroxyapatite). Those of ordinary skill in the art will readily appreciate other art-recognized techniques that would fall within this category. Elution strategies to separate the different products should not only be limited to pH variation, but could also encompass, by way of non-limiting and non-exhaustive example, cation-exchange separation techniques using step variation of salt concentration such as NaCl concentration or the concentration of other inorganic salts (e.g., inorganic salt combinations from the Hofmeister series of ions), Arginine and other amino acids such as histidine, proline, phenylalanine, tyrosine, tryptophan, and glycine concentration, use of mild denaturing agents such as, for example, Polysorbate 20, Polysorbate 80, Polyethylene glycol 2000, Polyethylene glycol 8000, Triton X-100, CHAPS, NP-40, and other ionic, non-ionic and/or zwitterionic surfactants, and so on.

LambdaFabSelect Chromatography Step: An anti-IL-6Rc/IL-6RC κλ-body bispecific IgG antibody was purified using LambdaFabSelect affinity chromatography media (GE Healthcare). The heavy and light chain amino acid sequences of the anti-IL-6Rc/IL-6RC κλ-body bispecific IgG antibody are shown below:

```
Anti-IL6RC VKappa light chain
                                                  (SEQ ID NO: 4)
EIVLTQSPATLSLSPGERATLSCRASQSVSSYLAWYQQKPGQAPRLLIYDASNRATGIPARFSG
SGSGTDFTLTISSLEPEDFAVYYCQQWLPTTPATFGQGTKVEIKRTVAAPSVFIFPPSDEQLKS
GTASVVCLLNNFYPREAKVQWKVDNALQSGNSQESVTEQDSKDSTYSLSSTLTLSKADYEKHKV
YACEVTHQGLSSPVTKSFNRGEC Anti-IL6RC VLambda light chain
                                                  (SEQ ID NO: 7)
QSALTQPASVSGSPGQSITISCTGTSSDVGGYNYVSWYQQHPGKAPKLMIYEVSNRPSGVSNRF
SGSKSGNTASLTISGLQAEDEADYYCSSWDAEFRAVFGGGTKLTVLGQPKAAPSVTLFPPSSEE
LQANKATLVCLISDFYPGAVTVAWKADSSPVKAGVETTTPSKQSNNKYAASSYLSLTPEQWKSH
RSYSCQVTHEGSTVEKTVAPTECS Common heavy chain
                                                  (SEQ ID NO: 6)
EVQLLESGGGLVQPGGSLRLSCAASGFTFSSYAMSWVRQAPGKGLEWVSAISGSGGSTYYADSV
KGRFTISRDNSKNTLYLQMNSLRAEDTAVYYCAKSYGAFDYWGQGTLVTVSSASTKGPSVFPLA
PSSKSTSGGTAALGCLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPG
```

After column loading at 20 mg/mL and a wash step with 50 mM Sodium Phosphate, 250 mM Sodium Chloride, pH 7.0 (5 column volumes), a pH step-elution was performed using a 50 mM glycine buffer adjusted at pH 3.0. The flow through and eluted fractions were collected and analyzed by absorbance measurement at 280 nm (using a NanoDrop UV-Vis spectrophotometer, Thermo Scientific) in order to determine product recovery, reduced and non-reduced SDS-PAGE (using Invitrogen Novex NuPAGE 12-well 4-20% gradient gels following manufacturer's guidelines) in order to determine the purity and composition of the samples and hydrophobic-high performance liquid chromatography (HIC-HPLC; method described below) in order to determine the ability of the purification process to separate the κλ-body bispecific IgG from the two monospecific antibody by-products.

HIC-HPLC method: In order to determine the relative proportions of the λ-MAb, κ-MAb and the κλ-body in a sample mixture, a HIC-HPLC (hydrophobic interaction chromatography) assay using a Dionex ProPac HIC-10 column was used. A descending gradient between 85 to 25% of ammonium sulfate was applied onto the column after the loading of the sample in order to elute the 3 species with high resolution, the κ-MAb eluting first, followed by the κλ-body and finally the λ-MAb. Peak area integration of the UV trace monitored at 280 nm was performed in order to determine the amount of each species.

Figure 4A:
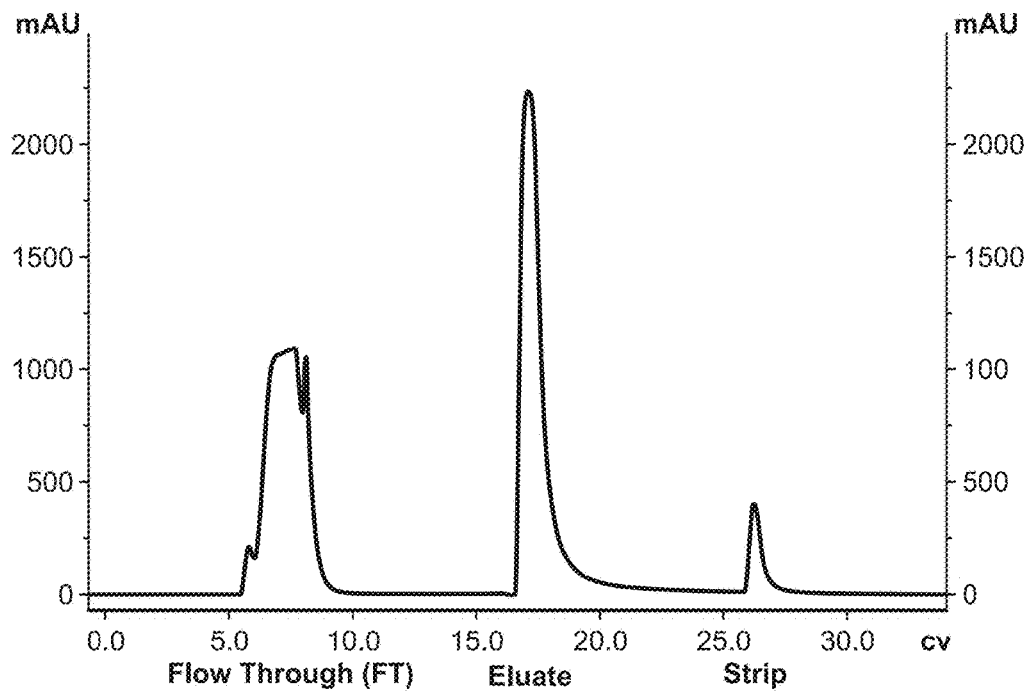
FIG. 4A is a graph depicting a representative UV-trace profile of LambdaFabSelect affinity chromatography using step pH elution.
Figure 4B:
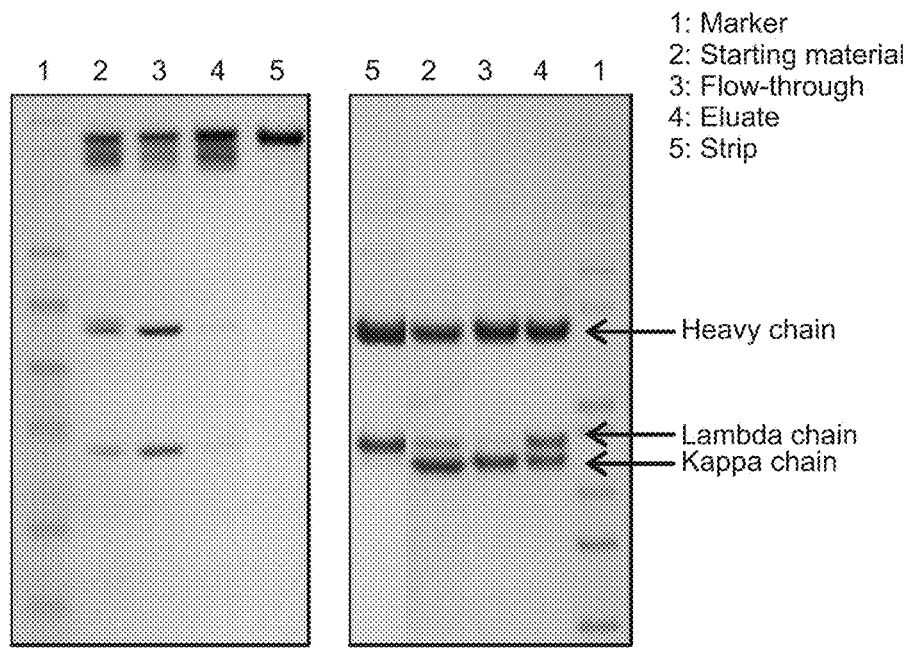
FIG. 4B is an illustration depicting non-reduced and reduced SDS-PAGE of LambdaFabSelect elution fractions.
Figure 4C:
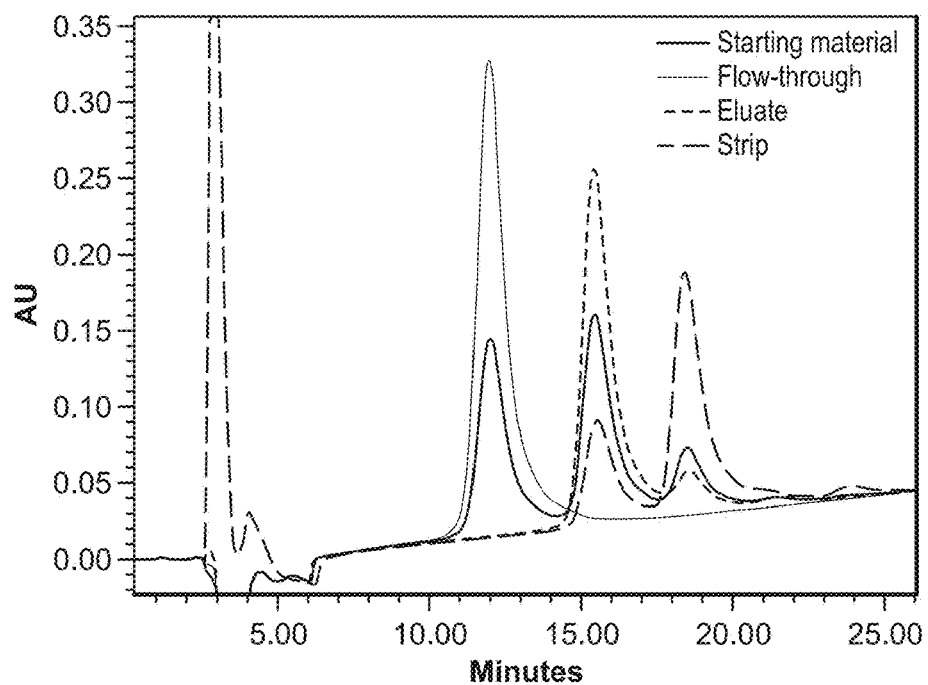
FIG. 4C is a graph depicting HIC-HPLC analysis of LambdaFabSelect elution fractions.

As shown by the UV trace in FIG. 4A, the pH step elution applied to the LambdaFabSelect chromatography resin allowed the purification of the κλ-body. Non-reduced SDS-PAGE analysis, shown in FIG. 4B, revealed the high purity of the purified fraction containing assembled full length antibodies as anticipated. Some free light chain products (monomer and dimer forms) were also detected by non reduced SDS-PAGE. The purified fraction was further characterized by integrating the peak areas of the HIC-HPLC chromatograms (FIG. 4C). The results summarized in Table 2 were in accordance with the SDS-PAGE analysis, demonstrating the vast abundance of the κλ-body (89.4%) in the eluate fraction at pH 3.0.

TABLE 2

UV peak integration of HIC-HPLC analysis of LambdaFabSelect bound fractions

| | % area | | |
|---|---|---|---|
| Samples | mono-λ | κλ-body | mono-κ |
| LambdaFabSelect flow-through | Not detected | Not detected | 100.0% |
| LambdaFabSelect pH 3.0 eluate | 89.4% | 10.6% | Not detected |
| LambdaFabSelect strip | 100.0% | Not detected | Not detected |

Free light chain reduction using Mep HyperCel™ mixed mode chromatography: To decrease manufacturing costs, the biotech/pharmaceutical industry is developing purification processes that omit the initial protein A-affinity chromatography step. Alternative purification solutions are therefore currently being explored. In particular, mixed-mode chromatography offers novel selectivity exploiting a combination of both ionic and hydrophobic interactions allowing for selective isolation of antibodies from the cell culture contaminants. These contaminants can include host cell proteins, cellular DNA, endotoxins, viruses, as well as antibody fragments. As described above, mammalian cells expressing recombinant antibodies also secrete non-assembled free light chains into the supernatant.

The present invention relates to the efficient removal of free light chains from monospecific and bispecific antibodies. In particular, chromatography conditions have been identified that are applicable for bispecific or monospecific monoclonal antibodies and free light chains. The present invention is illustrated by a method of reducing free light chain contaminants from the supernatant of a CHO cell line expressing a κλ-body (see FIG. 5A-5C). The method comprises the following steps: a) applying the cell culture supernatant to a solid chromatography mixed-mode resin (e.g., MEP HyperCel), b) eluting the monoclonal antibody with an acetate-buffered elution buffer at a pH 5.0 (eluate), and c) removing free light chains which are strongly bound to the resin at pH 2.1 (strip).

Figure 5A:
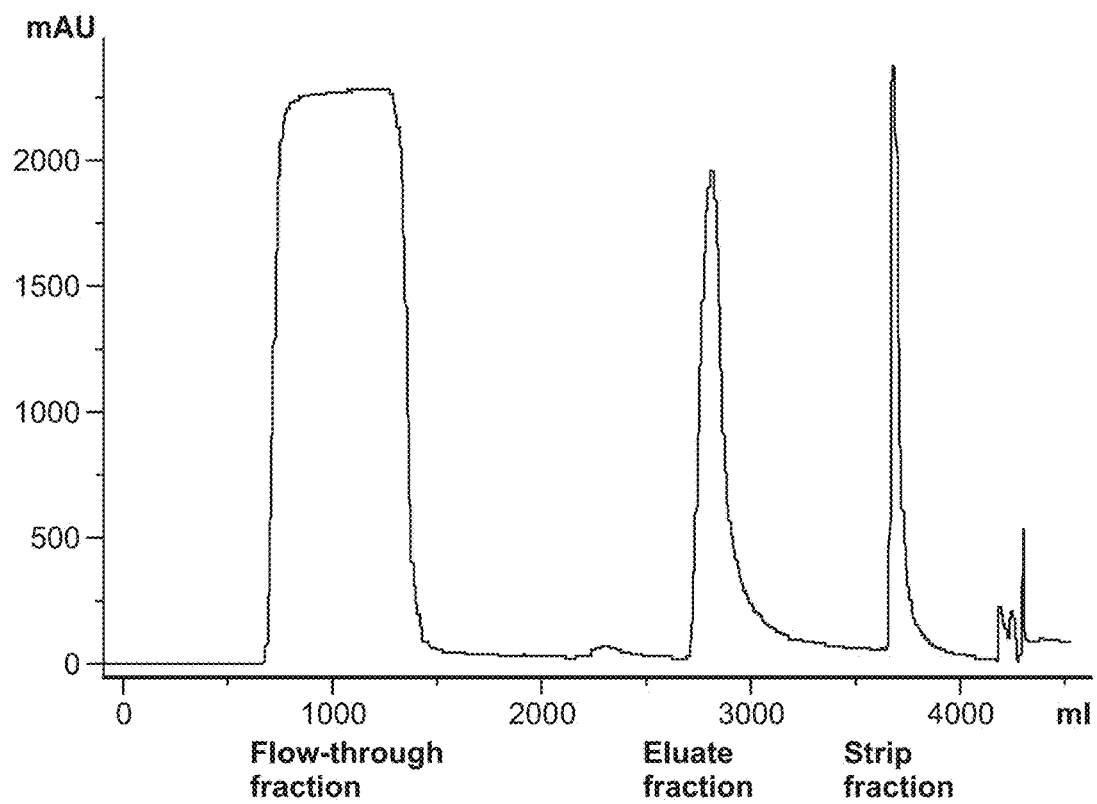
FIG. 5A is a graph depicting a representative UV-trace profile of Mep HyperCel™ mixed mode chromatography using step pH elution.
Figure 5B:
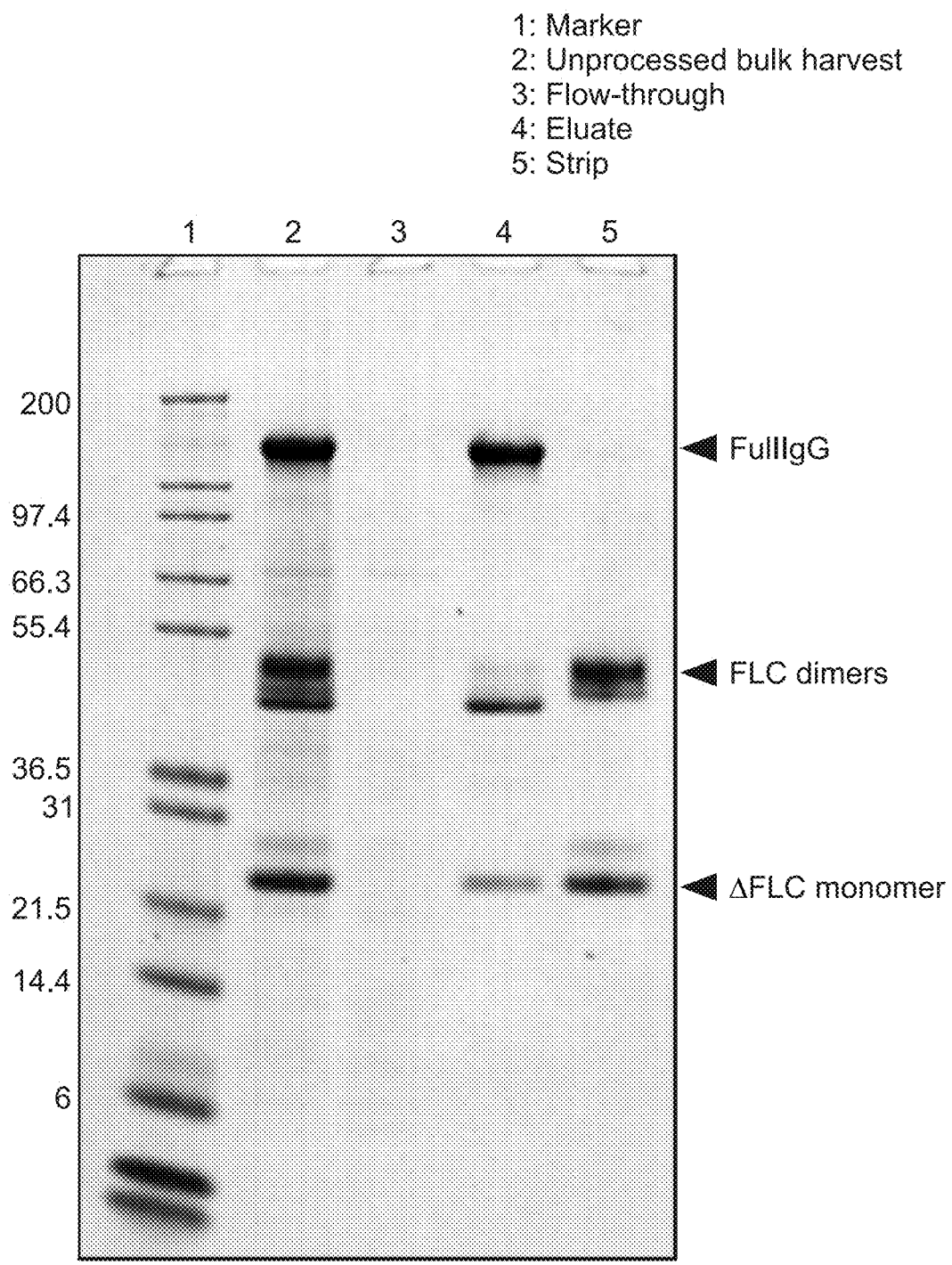
FIG. 5B is an illustration depicting non-reduced and reduced SDS-PAGE of Mep HyperCel™ elution fractions.
Figure 5C:
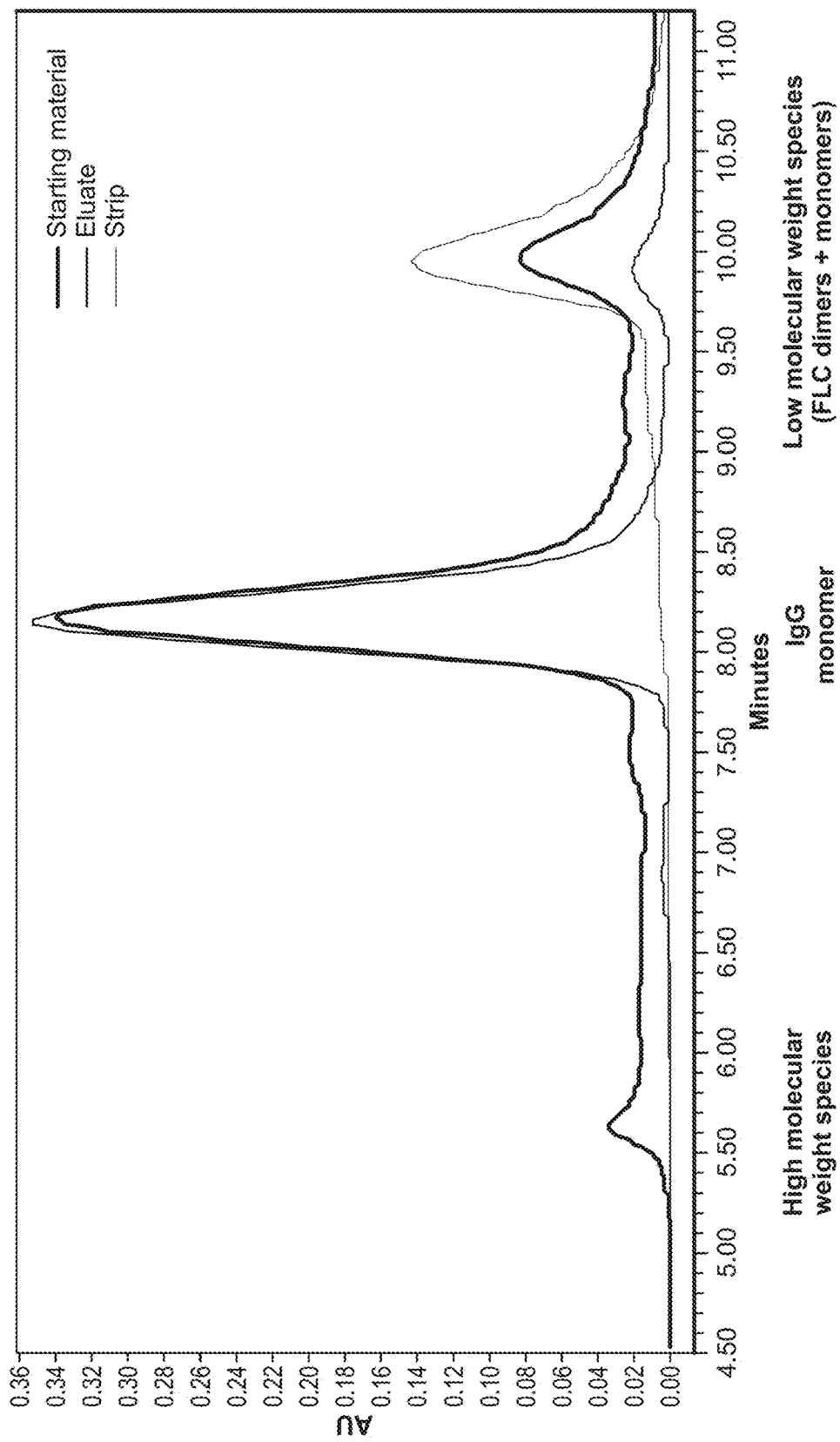
FIG. 5C is a graph depicting HIC-HPLC analysis of Mep HyperCel™ elution fractions.

FIG. 5A shows a representative MEP HyperCel chromatogram demonstrating the presence of FLC in the strip as determined by non-reduced SDS PAGE (FIG. 5B). SEC HPLC analysis confirmed efficient FLC removal from 60% in the cell culture supernatant down to 33% in the antibody eluate fraction (FIG. 5C) and Table 3 below.

TABLE 3

Analysis of Mep HyperCel ™ chromatography fractions by SEC-HPLC.

|  | High molecular weight species | IgG monomer | Free light chains |
|---|---|---|---|
| Unprocessed bulk harvest | 1.8% | 32.2% | 66.0% |
| Flow through | Not detected | Not detected | Not detected |
| Eluate | 0.9% | 66.1% | 33.0% |
| Strip | Not detected | Not detected | 100.0% |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of purifying a bispecific antibody consisting of two copies of a single heavy chain polypeptide and a first light chain comprising a kappa constant region and a second light chain comprising a lambda constant region (κλ-bodies), the method consisting of the steps of:
   (a) providing a mixed antibody composition comprising κλ-bodies; one or more monospecific monoclonal antibodies having two lambda light chains (λ-MAb); and one or more monospecific monoclonal antibodies having two kappa light chains (κ-MAb);
   (b) providing a separation means that has specific affinity for a kappa light chain constant region or a lambda light chain constant region;
   (c) contacting the separation means with the mixed antibody composition under conditions that allow for the mixed antibody composition to specifically bind the separation means;

(d) washing the separation means to elute impurities;
(e) eluting the κλ-bodies under conditions that allow for preferential detachment of the κλ-bodies thereby purifying the κλ-bodies.

2. The method of claim 1, wherein the separation means having specific affinity for kappa light chain constant region is
a resin, a membrane, a magnetic bead, a particle or a monolith coupled to a ligand having specific affinity for the kappa light chain constant region; and the separation means having specific affinity for lambda light chain constant region is
a resin, a membrane, a magnetic bead, a particle or a monolith coupled to a ligand having specific affinity for the lambda light chain constant region.

3. The method of claim 1, wherein the elution conditions comprise a step variation in the pH level.

4. The method of claim 1, wherein the elution conditions comprise a variation of the concentration of an amino acid in the composition.

5. The method of claim 4, wherein the amino acid is arginine, histidine, proline, phenylalanine, tyrosine, tryptophan and/or glycine.

6. A single step affinity chromatography method of purifying a bispecific antibody consisting of two copies of a single heavy chain polypeptide and a first light chain comprising a kappa constant region and a second light chain comprising a lambda constant region (κλ-bodies), the method consisting of:
(a) providing a mixed antibody composition comprising κλ-bodies; one or more monospecific monoclonal antibodies having two lambda light chains (λ-MAb); and one or more monospecific monoclonal antibodies having two kappa light chains (κ-MAb);
(b) providing a separation means, wherein the separation means is an anti-kappa light chain antibody, or an anti-lambda light chain antibody coupled to a solid support;
(c) contacting the separation means with the mixed antibody composition under conditions that allow for the mixed antibody composition to specifically bind the separation means;
(d) washing the separation means to elute impurities with a wash solution having a pH of about 7.0 or higher; and
(e) eluting specifically the κλ-bodies with an elution solution having a pH of about 3.0, thereby purifying the κλ-bodies.

7. The method of claim 6, wherein the solid support is a resin, a membrane, a magnetic bead, a particle or a monolith.

8. The method of claim 6, wherein the solid support is a highly cross-linked agarose.

* * * * *

SEQUENCE LISTING

```
<160> NUMBER OF SEQ ID NOS: 7

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4
<211> LENGTH: 215
<212> TYPE: PRT
<213> ORGANISM: Artificial Sequence
<220> FEATURE:
<223> OTHER INFORMATION: chemically synthesized

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Trp Leu Pro Thr Thr Pro
                85                  90                  95

Ala Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 5
<211> LENGTH: 218
<212> TYPE: PRT
<213> ORGANISM: Artificial Sequence
<220> FEATURE:
<223> OTHER INFORMATION: chemically synthesized

<400> SEQUENCE: 5

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Gln Ser Trp
                85                  90                  95

Asp Gly Asn His Ile Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 6
<211> LENGTH: 445
<212> TYPE: PRT
<213> ORGANISM: Artificial Sequence
<220> FEATURE:
<223> OTHER INFORMATION: chemically synthesized

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 7
<211> LENGTH: 216
<212> TYPE: PRT
<213> ORGANISM: Artificial Sequence
<220> FEATURE:
<223> OTHER INFORMATION: chemically synthesized

<400> SEQUENCE: 7

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Trp Asp Ala Glu
                85                  90                  95

Phe Arg Ala Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```